US006231852B1

(12) United States Patent
Bredesen

(10) Patent No.: US 6,231,852 B1
(45) Date of Patent: *May 15, 2001

(54) METHOD FOR REDUCING BCL-2 EXPRESSING CELLS RESISTANCE TO DEATH

(75) Inventor: Dale E. Bredesen, Rancho Santa Fe, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/707,055

(22) Filed: Sep. 3, 1996

Related U.S. Application Data

(63) Continuation-in-part of application No. 08/616,604, filed on Mar. 15, 1996, now abandoned, which is a continuation of application No. 08/154,281, filed on Nov. 18, 1993, now abandoned.

(51) Int. Cl.[7] .................. A61K 38/44; A61K 39/395; A61K 39/385; A01N 37/18
(52) U.S. Cl. ................... 424/94.4; 424/613; 424/617; 424/616; 424/175.1; 424/138.1; 424/174.1; 424/195.11; 514/2; 514/885; 435/240.2
(58) Field of Search ................. 435/240.2; 424/94.4, 424/613, 617, 616; 514/2, 885

(56) References Cited

U.S. PATENT DOCUMENTS

| | | | |
|---|---|---|---|
| 4,481,195 | * | 11/1984 | Rabin . |
| 4,939,178 | * | 7/1990 | Muller . |
| 5,002,755 | * | 3/1991 | Mitchell . |
| 5,677,135 | * | 10/1997 | Bredesen . |
| 5,681,711 | * | 10/1997 | Bredesen . |
| 5,834,457 | * | 11/1998 | Bredesen et al. . |

FOREIGN PATENT DOCUMENTS

| | | |
|---|---|---|
| WO94/27426 | 12/1994 | (WO) . |
| WO95/05750 | 3/1995 | (WO) . |

OTHER PUBLICATIONS

Hockenbery et al., "Bcl–2 is an inner mitochondrial membrane protein that blocks programmed cell death," Nov. 22, 1990, Nature, vol. 348, pp. 334–336.

Zhong et al., "BCL–2 Inhibits Apoptosis in Multiple Neural Cell Types," Abst. 25.11, Society for Neuroscience Abstracts, vol. 18, 1992.

Nuñez et al., "Deregulated Bcl–2 Gene Expression Selectively Prolongs Survival of Growth Factor–Deprived Hemopoietic Cell Lines," May 1, 1990, Journal of Immunology, vol. 144, No. 9 pp. 3602–3610.

Zhong et al., "bcl–2 inhibits death of central neural cells induced by multiple agents," May 1993, Proc. Natl. Acad. Sci., vol. 90, pp. 4533–4537.

Mah et al. "The Protooncogene bcl–2 Inhibits Apoptosis in PC12 Cells," 1993, J. Neurochem, vol. 60, No. 3, pp. 1183–1185.

Garcia et al., "Prevention of Programmed Cell Death of Sympathetic Neurons by the bcl–2 Proto–Oncogene," Oct. 9, 1992, Science, vol. 258, pp. 302–304.

Martinou et al., "The bcl–2 Proto–Oncogene Protects Neurons From Naturally Occurring Cell Death In Vivo," Abst. 279.16, Society for Neuroscience Abstracts, vol. 19, 1993.

Merry et al., "bcl–2 protein expression is widespread in the developing nervous system and retained in the adult PNS," Development 120, 301–311 (1994).

Allsopp et al., "The Proto–Oncogene bcl–2 Can Selectively Rescue Neurotrophic Factor–Dependent Neurons From Apoptosis," Cell, vol. 73, 295–307, 1993.

Kane et al., "Bcl–2 Inhibits Neural Cell Death by Decreasing the Production of Reactive Oxygen Species," Abst. 279.17, Society for Neuroscience Abstracts, vol. 19, 1993.

Zhong et al., "Bcl–2 blocks glutamate toxicity in neural cell lines," Molecular Brain Research, 19 (1993) 353–355.

Wood et al, Biochemistry: A Problems Approach (1980) pp 232–233.*

DeVita et al, Cancer: Principles and Practice of Oncology, J.B. Lippincott Co., Philadelphia (1993) p 282.*

Dornand et al, Immunology: 68(3) pp 384–391 (1989).*

Hockenberry et al PNAS: 88 pp 6961–6965 (1991).*

Clark et al, Infection and Immunity, (1983) 39(1) Abstract.*

* cited by examiner

*Primary Examiner*—Mita Minnifield
(74) *Attorney, Agent, or Firm*—Gray Cary Ware & Freidenrich LLP; Lisa A. Haile

(57) ABSTRACT

Methods for controlling cell death when the cell is exposed to one or more potentially lethal cellular insults. In one method, cell death is inhibited by introducing a reactive oxygen species limiter into the cell which prevents the build up of lethal levels of reactive oxygen species when the cell is exposed to a cellular insult. In another method, cell death is promoted in cancer cells or other proliferating cells which are naturally resistant to lethal cellular insults. The method involves neutralizing reactive oxygen species limiters, such as bcl-2, which occur naturally in cancer cells and which prevent the build up of reactive oxygen species within the cancer cells when they are exposed to lethal cellular insult. Neutralizing the reactive oxygen species limiter leaves the cancer cell unable to protect itself when cellular insult causes increases in the level of reactive oxygen species. The result is an increase in cell death.

18 Claims, 4 Drawing Sheets

METHOD FOR REDUCING BCL-2 EXPRESSING CELLS RESISTANCE TO DEATH

This application is Continuation-in-Part Application of U.S. application Ser. No. 08/616,604, filed Mar. 15, 1996, now abandoned, which is a continuation of U.S. application Ser. No. 08/154,281, filed Nov. 18, 1993, now abandoned.

This invention was made with support under Grant No. NS27812 from the National Institutes of Health. Accordingly, the United States Government has certain rights in this invention.

BACKGROUND OF THE INVENTION

1. Field of the Invention

The present invention relates generally to methods for controlling cell death when a cell is exposed to one or more potentially lethal cellular insults. More particularly, the present invention is directed to the discovery that the cellular production of reactive oxygen species plays an important role in apoptosis or necrosis of a cell when it is exposed to a potentially lethal insult. By controlling the production of reactive oxygen species, cells may be saved which would otherwise die due to the production of excessive reactive oxygen species. Alternatively, cells which resist intentional lethal insults may be rendered more susceptible to death by limiting their ability to prevent production of reactive oxygen species when they are subjected to such intentional insults.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

The phenomenon of cell death has been, and continues to be, the subject of a great deal of investigation. Many studies have been made to ascertain, identify and understand the mechanism(s) involved in cell death. Researchers have hoped that once the underlying mechanisms of cell death are understood that it will then be possible to construct procedures for controlling cell death. This would allow researchers to prevent cells from dying which otherwise would die when exposed to a potentially lethal cellular insult. Conversely, researchers could utilize their knowledge of the mechanism of cell death to hasten death of cancer cells or other undesirable cells which resist death even when subjected to a variety of cellular insults which normally would be lethal.

Some of the research regarding the mechanisms of cell death have centered around the identification and study of proteins which appear to play a role in inhibiting cell death when cells are exposed to potentially lethal insults. An example of such a protein is bcl-2. The protooncogene bcl-2 was discovered by translocation analysis of B-cell lymphomas (1). Subsequently it was reported that its protein product, bcl-2, is targeted to the inner membrane of mitochondria and that apoptosis of B cells, induced by the withdrawal of serum and growth factors, is inhibited by bcl-2 (2). The normal function of bcl-2 is unknown, as is the mechanism by which bcl-2 inhibits apoptosis. Furthermore, bcl-2 has little homology with other known proteins except the Epstein-Barr virus protein BHRF1 [for which no function is known (3)], although some homology to ras has been suggested (4).

Bcl-2 inhibits apoptosis in only a subset of hematopoietic cells. Bcl-2 has also been reported to inhibit the death of sympathetic neurons cultured in the absence of NGF (8).

There is a present and continuing need to discover and investigate the mechanism(s) which are involved in cell death. Once an understanding of a given cell death mechanism is understood, it would be desirable to be able to use this understanding to develop methods for controlling cell death. The control of cell death would not only allow one to prolong the life of desirable cells, but would also allow one to shorten the life of undesirable cells.

SUMMARY OF THE INVENTION

In accordance with the present invention, methods are provided for controlling cell death when the cell is subjected to one or more potentially lethal cellular insults. The present invention is based upon the discovery that an important aspect of both apoptotic and necrotic cell death is the production of reactive oxygen species. The increase in reactive oxygen species which occurs in normal neural cells when they are exposed to cellular insults results in cell death. It was discovered that cell death can be inhibited or avoided entirely if the increase in reactive oxygen species is prevented or at least limited.

As one feature of the present invention, bcl-2 protein is introduced into neural cells which are naturally lacking in this protein. It was discovered that bcl-2 is effective in preventing the production of lethal levels of reactive oxygen species within the cells when they were subjected to cellular insult. The bcl-2 protein was introduced into the cell by infecting the cell with a genetically engineered vector that was capable of expressing bcl-2.

Bcl-2 and related proteins may be used to inhibit cell death during exposure of cells to a variety of cellular insults. Cellular insult situations where the use of bcl-2 inhibits cell death include: withdrawal of serum or growth factor; withdrawal of glucose; exposure to calcium ionophore; membrane peroxidation; free radical-induced damage; and treatment of the cell to reduce its ability to protect itself from oxidative injury (e.g. exposure of cell to enzyme inhibitors such as buthionine sulfoximine).

As another feature of the present invention, cells which naturally include bcl-2 or other proteins which provide protection against oxidative cellular insults may be treated to remove the protection provided by such proteins. This is accomplished in accordance with the present invention by treating the cell with reductants and/or metal chelators which neutralize the effect of the protective protein. The resulting unprotected cell may then be killed by exposure to a selected insult protocol.

The invention is well-suited for increasing the susceptibility of cancer cells to attack by chemotherapy. Many cancer cells include protective compounds, such as bcl-2, which are necessary to the mechanism which protects the cancer cells against death due to oxidative injury. In accordance with the present invention, cancer cells may be treated to neutralize the protective compounds. This eliminates the cancer cells protective mechanism and renders it susceptible to attack by agents which cause oxidative injury due to the production of reactive oxygen species.

The above discussed and many other features and attendant advantages of the present invention will become better understood by reference to the following detailed description when taken in conjunction with the accompanying drawings.

DETAILED DESCRIPTION OF THE PREFERRED EMBODIMENTS

Figure 1:
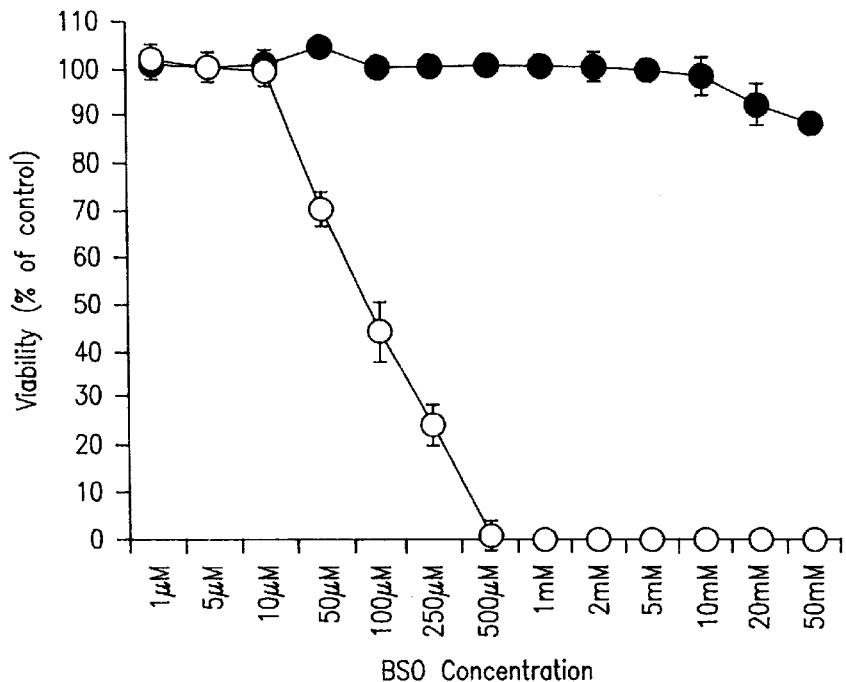
FIG. 1. Neural cell death in response to BSO. Solid circles, GT1–7 cells expressing bcl-2; open circles, control cells lacking bcl-2 expression. Each data point shows the mean of quadruplicate cultures with standard deviations. The experiment was performed six times. Error bars of less than 2% are embedded in the symbols. GT1–7 cells were infected with a recombinant retrovirus (pBP-bcl-2) or a control retrovirus, both constructed and infected as described (A2). Immunocytochemistry demonstrated that >98% of the selected cells expressed bcl-2, whereas the control cells did not express bcl-2. Cells were plated at a density of $10^5$ cells per well in poly-L-lysine-coated 96-well tissue culture plates (Costar) in Dulbecco's modified Eagle's medium (DMEM) with 10% fetal bovine serum. The L-buthionine-[S,R]-sulfoximine (Sigma) was dissolved in medium to make a 100 mM stock. BSO was added at the concentrations indicated, incubated for 24 hours, then removed and replaced by fresh medium. Cell viability was determined 24 hours later by formazan production from diphenyltetrazolium salt (MTT assay, as modified by Hansen et al.) (A20).

The present invention is based on the discovery of the mechanism by which cell death is inhibited by certain proteins when the cells are subjected to a variety of cellular insults. Specifically, it was discovered that bcl-2 and other related protective proteins prevent the production of reactive oxygen species in cells when they are subjected to cellular insults which otherwise would produce lethal levels of such reactive oxygen species in the cell.

This discovery allows one to provide methods for controlling cell death by altering the cells natural ability to control the production of reactive oxygen species in response to cellular insults. For example, the death of cells may be inhibited by introducing into the cell a reactive oxygen limiter, such as bcl-2. The bcl-2 enhances the cells ability to limit the production of reactive oxygen species to sub-lethal levels when the cell is exposed to various cellular insults.

Another exemplary method involves increasing cell death in the face of cellular insults by removing or neutralizing the cells natural supply of bcl-2 or other reactive oxygen limiter. This type of method is well-suited for use in connection with cancer treatment where the removal of a cancer cells natural supply of bcl-2 results in an increse in cell death during intentional cellular insults.

When used in this specification, the term reactive oxygen species means hydrogen peroxide, hydroxyl radicals, superoxide, nitric oxide and any of the other agents which are known to participate in oxidative injury to cells. The term reactive oxygen limiter is intended to mean bcl-2, p35, superoxide dismutase (Cu/Zn and Mn) and any of the other known proteins which are effective in limiting the ability of a cell to produce reactive oxygen in response to cellular insults. The type of cellular insults to which the cells are subjected include: withdrawal of serum or growth factor; withdrawal of glucose; membrane peroxidation; free radical attack; calcium ionophore addition, toxin insult (e.g. mercury), beta-amyloid treatment and glutamate treatment.

A first aspect of the present invention involves treating cells to inhibit cell death when the cell is exposed to cellular insults. The method involves introducing bcl-2 or other reactive oxygen limiter into the cell in accordance with any of the known procedures for introducing foreign matter into a cell. Preferably, the bcl-2is produced in the cell by a vector which has been genetically engineered to express the bcl-2 protein. The use of expression vectors to express a wide variety of proteins within a host cell are well-known procedures which will not be described in detail other than in the examples which follow.

The type of cells which are amenable to the method of the present invention include neural cells and any other cell which includes cellular mechanisms which produce reactive oxygen species when the cell is subjected to cellular insults.

The amount of reactive oxygen limiter which is produced in the cell in order to inhibit cell death will depend upon a number of parameters including cell type, insult type and severity, the vector used to express the limiter and the type of limiter used (e.g., which species are limited). The particular expression vector to be used to express a sufficient amount of reactive oxygen limiter can be determined by routine experimentation. Any expression vector system is suitable provided that sufficient reactive oxygen limiter is produced to protect the cell against excessive levels of reactive oxygen species in accordance with the present invention.

Another aspect of the present invention involves the treatment of proliferating cells, such as cancer cells, to increase their susceptibility to intentional cellular insults. The preferred method involves treating the cancer cell with a neutralizing agent which is capable of inactivating bcl-2 or other reactive oxygen species limiter which is naturally present in the cell. The elimination of the protective protein makes the cell more easily killed by the intentional cellular insults which are part of cancer chemotherapy. Exemplary tumors include metastatic prostatic carcinoma, breast carcinoma, oat cell carcinoma of the lung and neuroblastoma.

Exemplary procedures for treating proliferating cells to reduce their ability to limit the production of reactive oxygen species are as follows: where cancer cells express bcl-2 (prostatic, neuroblastoma, B-cell lymphoma) preferred neutralizing agents are metal chelating agents, reducing agents and mitochondrially-active agents. Preferred exemplary metal chelators to be used in accordance with the present invention include TPEN (N,N,$N^1$,$N^1$-tetrakis (2-pyridylmethyl) ethylene diamine) and desferrioxamine.

Preferred reducing agents to be used to treat cancer cells expressing bcl-2 include BHA (butylated hydroxyanisole) and BHT. Similarly, anti-neoplastic agents requiring reduction for activation would be enhanced in toxicity for bcl-2 expressing tumors.

Preferred mitochondrially-active agents include oligomycine and dinitrophenol.

Treatment protocols involve absorbing the metal chelator, reducing, or mitochondrially-active agent into the cell. For example, TPEN may be infused into cell cultures in vitro to provide a final concentration of from 1 $\mu$m to 10 mM. Preferably, the final concentration of TPEN in the cell culture is about 100 $\mu$M. The resultant absorption of TPEN into the cells neutralizes bcl-2 and eliminates the cell's protective mechanism against oxygen species. The reducing agent BHA, on the other hand, may for example be infused into cell cultures in vitro to provide a final concentration of from 0.1 to 10 mM. Preferably, the final concentrations of BHA is about 1 mM. Mitochondrially-active agents may also be infused into cell cultures. Oligomycin may be infused, for example, to a final concentration of from 1 to 100 $\mu$g/ml. Preferably the final concentration of oligomycin is about 20 $\mu$g/ml. Dinitrophenol is preferably infused to provide a final concentration of from 0.1 to 1000 $\mu$M. Most preferably, dinitrophenol is infused to a final concentration of about 100 $\mu$M.

In vivo treatment protocols require that the neutralizing agent be introduced directly into the cancer cells to limit toxic side effects. For cancerous tumors, the neutralizing agent may be injected directly into the tumor. Targeting vehicles conventionally used to target compounds to various cancer cells may also be used. The amount of neutralizing agent which is needed in vivo to sensitize cancer cells can be determined by routine experimentation for each patient. The dose is initially kept low (i.e. 1 mg per kg body weight) and then slowly increased until cell death in response to a selected cellular insult is achieved.

The following are examples of practice of the present invention:

EXAMPLE 1

In the following example, a neural cell line (CSM14. 1) was infected with a retrovirus which expressed bcl-2 protein. The CSM14. 1 cells which expressed bcl-2 were isolated and then subjected to various cellular insults. All of the various insults caused cell death in control cells. However, the cells expressing bcl-2 did not die or suffer reduced rates of cell death when subjected to the same cellular insults. Details of this example are as follows:

Cell Culture and Expression Constructs:

CSM14. 1 cells (9) were grown in Dulbecco's modified Eagle's medium (DMEM) with 10% fetal bovine serum (FBS, heat inactivated) at 34° C. or 39° C. in 5% $CO_2$. PC12 cells were maintained as described (7). The derivation of the plasmid pBabe puro-bcl-2, control plasmid pBabe puro, and high-titer retroviral producers was also as described (7). Following infection with recombinant retroviruses, cells stably infected were selected in puromycin (7 $\mu$g/ml). Immunocytochemical detection of the expression of bcl-2 was as described (7).

Viability in serum-free medium and in A23187 was assayed as described (7). To determine the effect of glucose starvation, cells were washed three times in Locke's solution (154 mM NaCl/5.6 mM KCl/2.3 MM $CaCl_2$/1.0 mM $MgCl_2$/3.6 mM $NaHCO_3$/5 mM Hepes) (11) before plating on 24-well plates in Locke's solution with 2% FBS (for CSM14.1 cells) or 1% horse serum plus 1% FBS (for PC12 cells). For the control group, cells were grown in the same solution with 40 mM glucose. To assess cell survival after the addition of the lipid peroxidizing agent tert-butyl hydroperoxide (t-BOOH) (12, 13), cells were grown in serum-containing medium with 0.5 $\mu$M t-BOOH. The t-BOOH was added at 8-hour intervals.

Assessment of Apoptosis:

Internucleosomal fragmentation of DNA was determined as described (7). For whole-cell assessments of apoptosis, 2 $\mu$l of acridine orange (100 $\mu$g/ml) and 2 $\mu$l of ethidium bromide (100 $\mu$g/ml) were mixed on a microscope slide. Twenty microliters of cell suspension ($10^6$ cells per ml) was then placed on the slide, covered with a coverslip, and observed with a Zeiss Axio-vert fluorescence microscope.

Intracellular Biochemical Measurements:

The levels of adenosine triphosphate were determined by the firefly luciferase method, as described (14). Measurement of intracellular free calcium was as described in detail (15). For quantitation of oxygen free radical species, in situ fluorescence measurements of cells loaded for 15 minutes with 3,7-dichlorofluorescein diacetate (DCF-DA) were obtained using a Cytofluor 2300 plate scanner (Millipore). Extent of oxidation was determined using known concentrations of oxidized DCF.

RESULT

Immunocytochemistry following selection of retrovirally infected cells (16) demonstrated expression of bcl-2 in nearly every cell infected with the bcl-2 recombinant retrovirus, with some cell-to-cell variability. Staining predominated in the perinuclear and cytoplasmic regions, appearing similar to that described for the expression of bcl-2 in Spodoptera frugiperda cells (17). Cells that had been infected with a recombinant retrovirus also expressing the puromycin-resistance gene but lacling bcl-2, showed no staining with the same antibody.

The expression of bcl-2 did not alter cell morphology, either in the undifferentiated or in the differentiated state. Neuritic outgrowth and development of reftractile somata were retained in bcl-2 expressing neural cells. Growth rate at the permissive temperature of 34° C. was also unaffected by the expression of bcl-2, with the doubling time of control cells being 24±3.6 hours and of bcl-2 expressing cells being 23±1.8 hours (proliferation did not occur in either group in the differentiated state).

In contrast to its lack of effect on growth or differentiation, bcl-2 expression markedly enhanced the survival of cells that had undergone any of several different insults. Serum withdrawal led to apoptotic neural death in the control cells but not those expressing bcl-2; this occurred at the permissive and restrictive temperatures. Mitosis virtually ceased in the bcl-2 expressing cells following the withdrawal of serum, but apoptosis did not occur. Similarly, the calcium ionophore A23187 induced cell death in the control cells, but little cell death occurred in bcl-2 expressing cells. Glucose withdrawal also induced some cell death in the bcl-2 expressing cells but affected the control cells to a much greater extent. This differential was present for PC12 pheochromocytoma cells as well as conditionally immortalized nigral neural cells [the effect of serum withdrawal, NGF withdrawal, and calcium ionophore treatment on bcl-2-expressing PC12 cells has been reported (7)]. When the cells were exposed to the membrane peroxidizing agent t-BOOH (12, 13) or to the inducer of free radical formation menadione (18), a prolongation of cell survival occurred in the bcl-2-expressing cells.

To explore potential mechanisms for the inhibition of neural cell death by bcl-2, intracellular free calcium was imaged and quantitated in conditionally immortalized nigral neural cells and PC12 cells expressing bcl-2 as well as in control cells. No differences were observed between bcl-2 expressors and control cells in resting concentration of free calcium or in peak or plateau levels following A23187 or ionomycin treatment. Serum withdrawal did not result in a measurable change in intracellular free calcium in any of the cell groups within the first 6 hours, the time at which apoptosis is well advanced in these cells, as demonstrated by DNA fragmentation (7) [trypan blue exclusion, however, does not occur until apoptosis is complete and secondary necrosis has begun (19)].

Resting lymphocytes undergo apoptosis by a mechanism dependent on poly(ADP-ribose) synthetase (10), resulting in severe reductions in cellular NAD levels; added nicotinamide (1–5 mM) increases NAD levels and inhibits apoptosis in noncycling lymphocytes. Therefore the effect of nicotinamide on apoptosis in conditionally immortalized neural cells was evaluated. Nicotinamide at 1–15 mM imparted no resistance to apoptosis in these cells, suggesting a different underlying mechanism in the two cell types.

Since growth factors such as NGF and platelet-derived growth factor (PDGF) inhibit apoptosis in some neural cells (20) and in oligodendroglial precursors (21), respectively, it was conceivable that the effect of bcl-2 expression might be mediated indirectly, via the secretion of a cellular survival factor. Therefore, the effect of conditioned medium from bcl-2 expressing cells was assayed. No significant difference was observed between the effect of conditioned medium from bcl-2 expressing cells and the control cells on the death of PC12 cells induced by withdrawal of serum.

Isolated thymocyte nuclei undergo apoptosis when bathed in calcium-containing medium; this effect is blocked by calcium chelation and by endonuclease inactivation (22). These findings have led to the hypothesis that apoptosis may be mediated by a specific calcium-activated endonuclease (23). Therefore, to determine whether bcl-2 primes the nucleus to resist apoptosis (e.g., by altering the expression of calcium-activated endonuclease), nuclei were isolated from bcl-2 expressing cells and control cells and then exposed to 2 mM calcium in the presence or absence of EGTA. Nuclei from both cell groups demonstrated internucleosomal DNA cleavage in the presence of calcium but not in the presence of EGTA.

The targeting of bcl-2 to the inner membrane of mitochondria (2) suggests that bcl-2 may have an effect on oxidative phosphorylation. Our studies showed no significant difference between the oxygen consumption (per viable cell) of control cells and bcl-2 expressors, prior to or following the withdrawal of serum (7). However, if bcl-2 affects the coupling of oxygen consumption to ATP formation, then ATP levels in control and bcl-2 expressing cells might differ markedly despite similar oxygen consumption. Therefore, levels of ATP were measured in the cells prior to and following the withdrawal of serum. ATP levels fell ≈50% in the 24 hours following serum withdrawal, with similar decrements occurring in the bcl-2 expressing cells and control cells.

This example shows that bcl-2 inhibits a process that is central to neural cell death, whether the death is induced by serum and growth factor withdrawal, calcium ionophore, glucose withdrawal, membrane peroxidation, or at least one form of free radical-induced damage.

EXAMPLE 2

In the following example, the expression of bcl-2 in a second neural cell line (GT1–7) is shown to cause a reduction in the amount of reactive oxygen species which are produced when the cells are insulted by exposure to buthionine sulfoximine (BSO). This example shows that the mechanism of cell death in these neural cells is tied directly to the amount of reactive oxygen species produced during cellular insult. In accordance with the present invention, the expression of bcl-2 in the cell was found to reduce the amount of reactive oxygen species which were produced during cellular insult. The result was inhibition of cell death.

The details of the example are as follows:

GT1–7 cells were infected with a recombinant retrovirus (pBP-bcl-2) or a control retrovirus, both constructed and infected as described (A2). Immunocytochemistry demonstrated that >98% of the selected cells expressed bcl-2, whereas the control cells did not express bcl-2. Cells were plated at a density of $10^5$ cells per well in poly-L-lysine-coated 96-well tissue culture plates (Costar) in Dulbecco's modified Eagle's medium (DMEM) with 10% fetal bovine serum. The L-buthionine-[S,R]-sulfoximine (Sigma) was dissolved in medium to make a 100 mM stock. BSO was added at the concentrations indicated, incubated for 24 hours, then removed and replaced by fresh medium. Cell viability was determined 24 hours later by formazan production from diphenyltetra lium salt (MTT assay, as modified by Hansen et al.) (A20).

The hypothalamic neural cell line GT1–7 (A3) displayed a remarkable sensitivity to toxicity from buthionine sulfoximine (BSO), which was abrogated by the expression of bcl-2. BSO is a specific and essentially irreversible inhibitor of y-glutamylcysteine synthetase (A4) and thus decreases the intracellular concentration of reduced glutathione (GSH), a tripeptide involved in protecting the cell from oxidative injury. Although bcl-2 inhibits apoptosis, the death of GT1–7 cells induced by GSH depletion is necrotic. This finding demonstrates that bcl-2 does not inhibit apoptosis per se; rather, bcl-2 inhibits a cellular process that may result in apoptosis or necrosis.

Figure 2A:
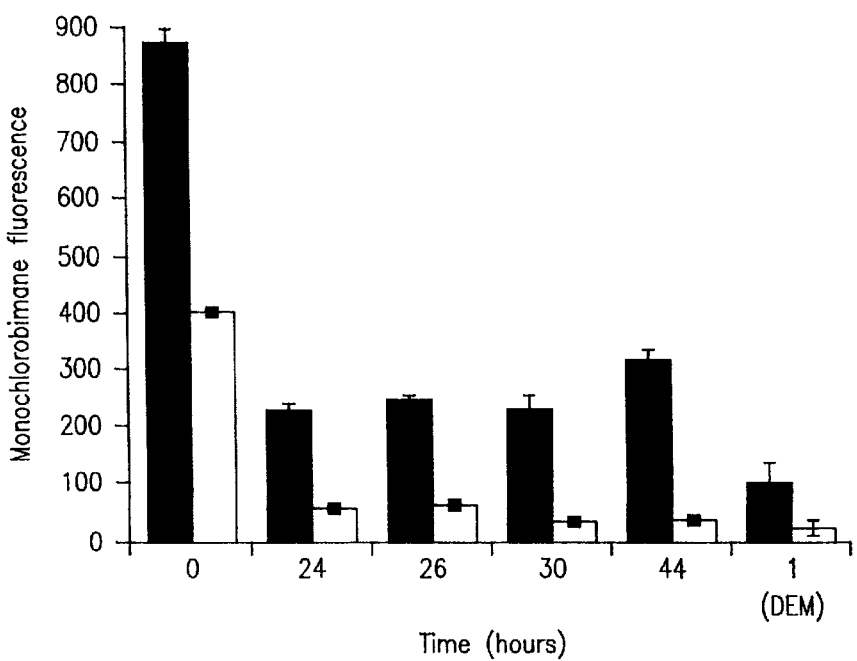
FIG. 2. (A) Cellular GSH in GT1–7 cells is increased in association with bcl-2 expression (solid bars) and falls during treatment with BSO or diethyl maleate (DEM). Bars show quantitated fluorescence of cells incubated with monochlorobimane, which fluoresces in the presence of GSH (A6). Data shown represent the average of quadruplicate cultures, and the experiment was repeated three times. Unfilled bars, control cells (GT1–7 lacking bcl-2 expression). Cells were assayed for GSH before BSO exposure (t=0), then exposed to 500 $\mu$M BSO for 24 hours, after which the medium was replaced with fresh medium, and GSH was again assayed (t=24 hours). Over the next several hours GSH was assayed until the control cells had died. Also shown are the GSH concentrations of cells treated with 1 mM DEM for 1 hour. (B) Viability of GT1–7 cells lacking bcl-2 expression (open circles) falls quickly after exposure to BSO for 24 hours. Viability of cells expressing bcl-2 (solid circles) remained high throughout the experiment. Each data point represents the average of quadruplicate cultures, with standard deviations shown (error bars of less than 2% are embedded in the symbols). The experiment was performed three times. (C) Viability of GT1–7 cells lacking bcl-2 expression (open circles) falls very quickly after treatment for 1 hour with 1 mM diethyl maleate at 23° C., whereas cells expressing bcl-2 (closed circles) remained viable after a reduction in GSH to less than 10% of their original concentration. Cellular GSH was measured with monochlorobimane (MCB, Molecular Probes) (A6). MCB (40 $\mu$M) was added to cells in 96-well plates and the cells incubated for 15 minutes, then fluorescence at 460 nm in response to excitation at 395 nm was quantitated with a Cytofluor 2300 plate reader (Millipore, Inc.). Cell death was quantitated by propidium iodine fluorescence (emission at 590 nm in response to excitation at 530 nm). Propidium iodide (Aldrich) was prepared as a 5 mM stock in water, diluted to 20 $\mu$M in medium, and added to cells, and fluorescence was read after 15 minutes of incubation. Total cell numbers were confirmed by Hoechst 33342 staining as described (A21).
Figure 2B:
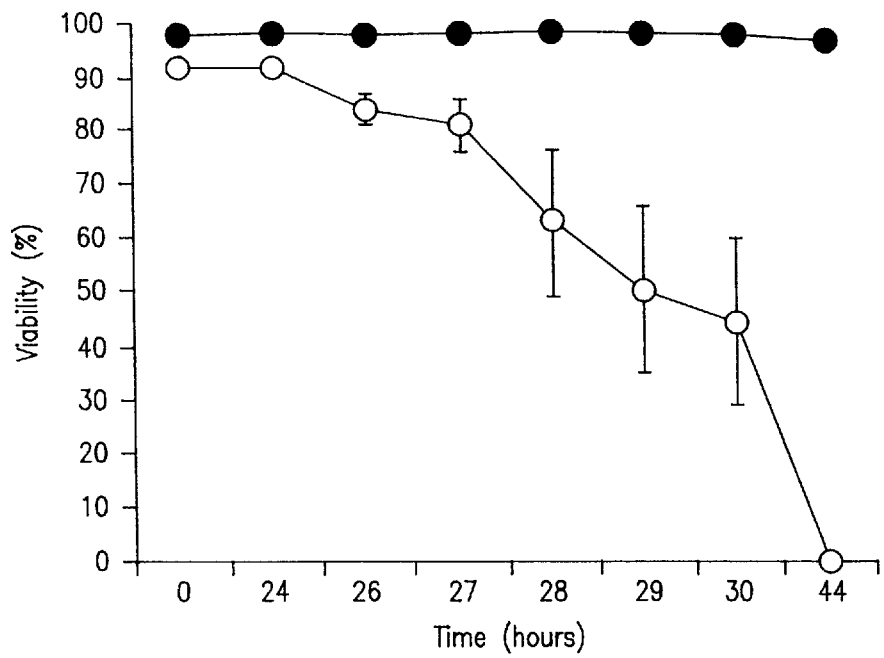

Treatment of GT1–7 cells with BSO led to cell death within 40 hours, with an $LD_{50}$ (median lethal dose) of ~100 μM (FIG. 1). Stable expression of bcl-2 by means of a retroviral vector raised the $LD_{50}$ about three orders of magnitude, to greater than 50 mM (FIG. 1). Measurement of intracellular GSH with monochlorobimane (A6) confirmed a decrement after exposure to BSO for both control and bcl-2 expressing cells (FIG. 2A). However, cells expressing bcl-2 had two or three times the basal concentrations of GSH and correspondingly higher concentrations during BSO treatment (FIG. 2A). To determine whether the survival of neural cells expressing bcl-2 was a result of the increase in GSH, diethyl maleate was used to bind the free sullhydryl groups of GSH (A7). After exposure to 1 mM diethyl maleate, cells expressing bcl-2, as well as control cells, had a decrease of more than 90% in GSH (FIG. 2A). Despite this, cells expressing bcl-2 survived (FIGS. 2, B and C), demonstrating that the increase in survival of bcl-2 expressing cells is not simply a result of the increase in total cellular GSH. Because neither diethyl maleate nor BSO rapidly depletes mitochondrial GSH (A8), cells were treted with ethacrynic acid, which depletes both cytosolic and mitochondrial GSH (A9). Treatment of GT1–7 cells with 200 μM ethacrynic acid resulted in the death of control cells with 24 hours, but bcl-2-expressing cells remained viable.

Figure 2C:
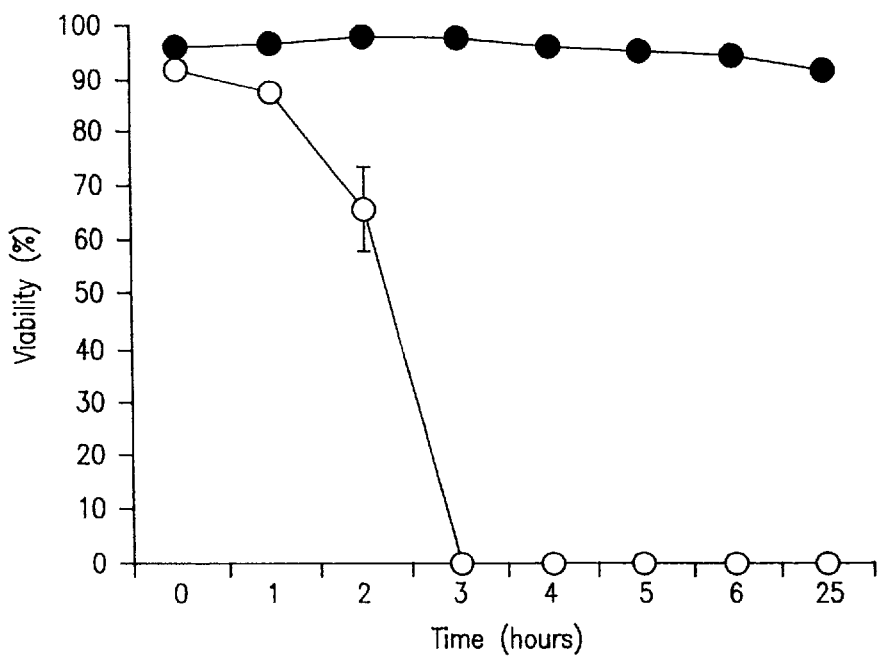
Figure 3:
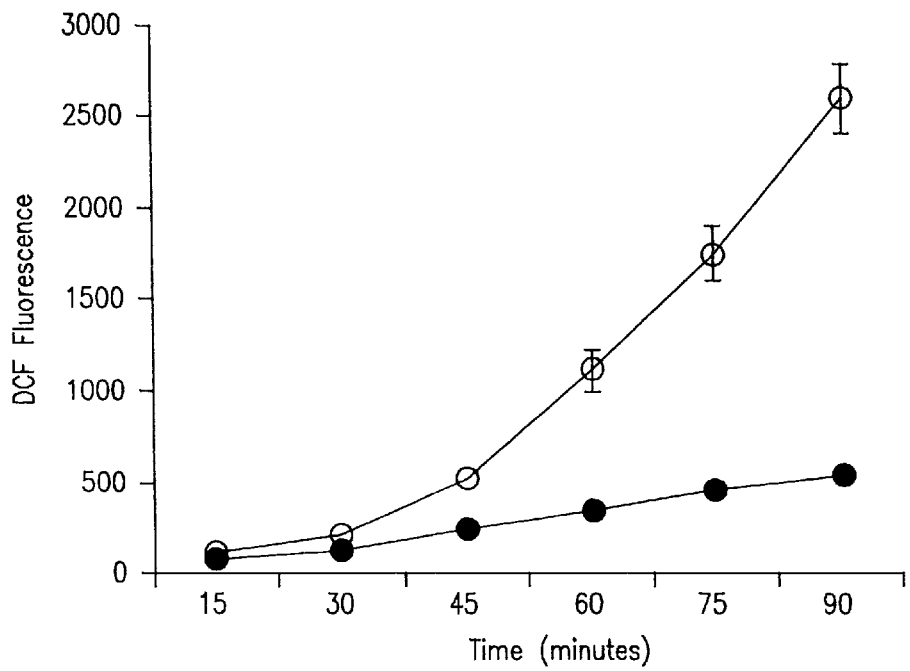
FIG. 3. Intracellular generation of reactive oxygen species in GT1–7 cells expressing bcl-2 (solid circles) or control transfectants (open circles) treated with 1 mM diethyl maleate. Cells were plated at a density of $10^5$ cells per well in a 96-well tissue culture plate (Nunc) that had been coated with poly-L-lysine (Sigma). Wells were washed three times with a modified Krebs-Ringer solution (KR, 20 mM Hepes, 10 mM dextrose, 127 mM NaCl, 5.5 mM KCl, 1 mM $CaCl_2$, and 2 mM $MgSO_4$, pH 7.4), then KR buffer containing DCF (1 $\mu$g/ml) (Molecular Probes) plus 1 mM diethyl maleate (Sigma) was added in a total volume of 100 $\mu$l. Plates were read on a Cytofluor 2300 plate reader, with an excitation wavelength of 485 nm and an emission wavelength of 530 nm, at 15 minute intervals for 90 minutes. Each point represents the average of triplicate wells with error bars included. This experiment was repeated six times with reproducible results; the one shown is representative. Error bars representing less than 50 DCF fluorescence units are embedded in the symbols.

Because the elevated GSH associated with bcl-2 might have resulted from decreased utilization of GSH, the fluorescent probe dichlorofluorescein diacetate (DCF) (A11) was used to measure the net intracellular generation of reactive oxygen species in diethyl-maleate-treated cells to determine whether bcl-2 effected a decrement in oxidative stress. This probe measures primarily hydrogen peroxide and hydroxyl radical (A11). By 90 minutes the DCF fluorescence of control cells had increased by a factor of 23 (FIG. 3); cells died between 2 and 3 hours (FIG. 2C). In contrast, the bcl-2-expressing cells showed only a modest increase in DCF fluorescence (FIG. 3) and the cells survived (FIG. 2C).

Figure 4A:
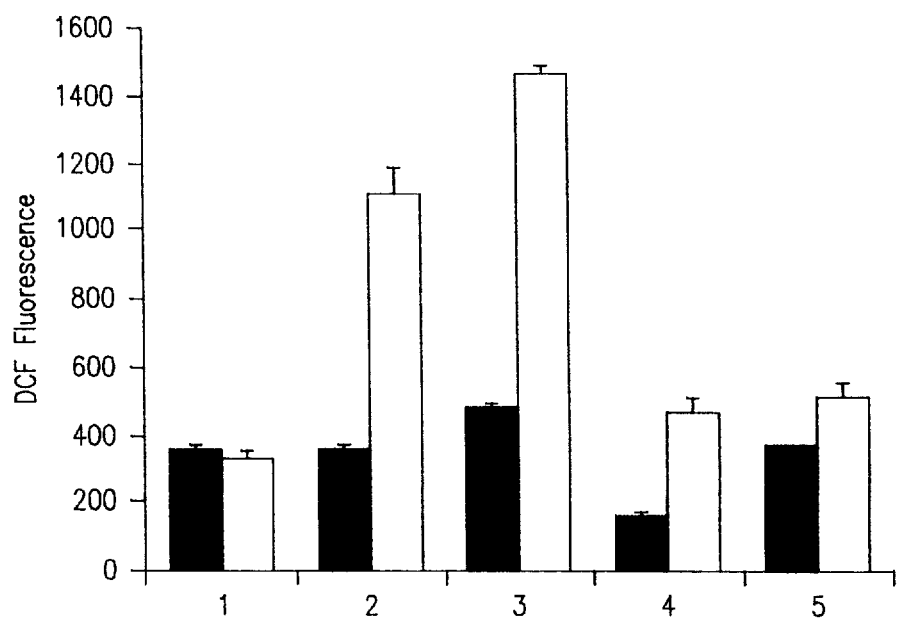
FIG. 4. (A) Modulation of intracellular generation of reactive oxygen species. Cells were treated as described in FIG. 3, but with the addition of either (1) KR and DCF only, (2) KR and DCF plus 1 mM diethyl maleate, (3) KR, DCF, and diethyl maleate plus 25 mM aminotriazole (Sigma), (4) KR, DCF, and diethyl maleate plus 100 $\mu$M desferrioxamine mesylate (Sigma). (Similar results were obtained with 25 $\mu$M diphenyl-p-phenylenediamine.) KR, modified Krebs-Ringer as described in FIG. 3; DCF (1 $\mu$g/ml). The bars represent the fluorescence recorded 60 minutes after the addition of diethyl maleate, DCF, and the various components. Each experiment was performed at least two times, and the data shown represent the average of triplicate wells with error bars included. Filled bars, bcl-2-expressing cells; unfilled bars, control transfectants. (B) Viability of bcl-2 expressing cells compared with control transfectants in response to various agents. Cells were plated at a density of $10^5$ cells per well in poly-L-lysine-coated 96-well plates (Nunc), then grown in high glucose (4.5 g/liter) DMEM plus 10% heat-inactivated fetal bovine serum in a 37° C. humidified incubator in 5% $CO_2$ and 95% air. After allowing the cells to adhere overnight, we removed the culture medium and replaced it with medium containing either (1) 500 $\mu$M BSO, assayed after 24 hours; (2) 500 $\mu$M BSO, assayed after 48 hours; (3) 500 $\mu$M BSO plus 25 mM aminotriazole, assayed after 24 hours; (4) 500 $\mu$M BSO plus 100 $\mu$M desferrioxamine mesylate, assayed after 48 hours; or (5) 500 $\mu$M BSO plus 1 mM ascorbic acid, assayed after 48 hours. (Similar results were obtained with 25 $\mu$M diphenyl-p-phenylenediamine.) Viability was determined either 24 or 48 hours later, as indicated, by two methods: the MTT assay (A20), which reflects the number of viable cells, and by quantitation of propidium iodide fluorescence, as a measure of cell death. For the fluorescence assay, we confirmed total cell numbers by lysing the cells with 50 $\mu$M digitonin, then adding propidium iodide (20 $\mu$g/ml). Fifteen minutes later, fluorescence was quantitated with a Cytofluor 2300 plate reader, with an excitation wavelength of 530 nm and an emission wavelength of 645 nm. Data generated by both assays were in good agreement and representative data are shown here. Data shown represent the average of triplicate wells with standard errors shown, and each experiment was performed at least two times. Filled bars, bcl-2-expressing cells; unfilled bars, control cells.
Figure 4B:
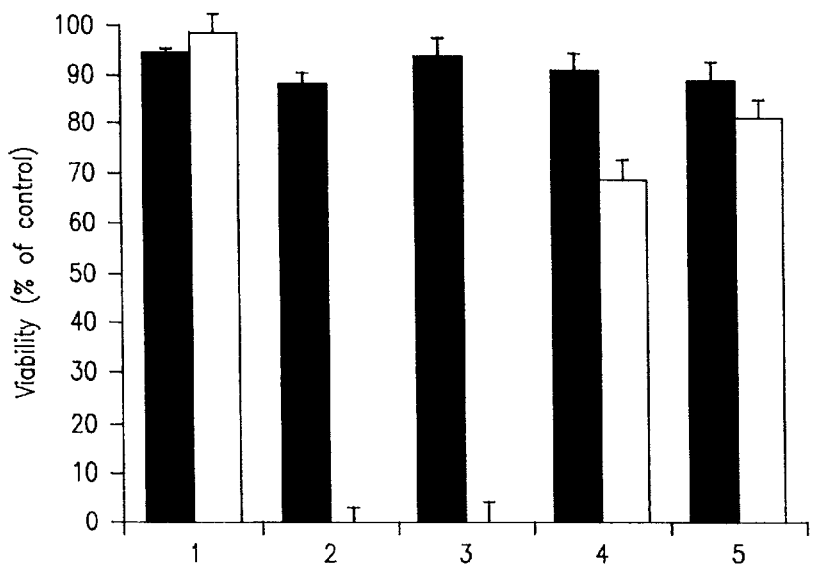

Similar results were obtained with ethacrynic acid treatment. To distinguish between a causal and noncausal association of neural cell death with reactive oxygen species in this system, the concentration of reactive oxygen species was manipulated with various compounds in conjunction with diethyl maleate and the effect on GT1–7 viability was examined. The addition of the iron chelator desferrioxamine (100 μM) (A12) reduced reactive oxygen species production as well as inhibited cell death induced by GSH depletion. The antioxidants ascorbic acid (1 mM) and N,N'diphenyl-p-phenylenediamine (25 μM) (A13) inhibited the BSO-induced death of control GT1–7 cells and reduced reactive oxygen species (FIG. 4A). When amino-triazole was used to inhibit catalase (A13) simultaneously with GSH depletion, control cells demonstrated a rise in reactive oxygen species above that associated with GSH depletion alone (FIG. 4A). Correspondingly, control cells died more quickly than cells that had only been depleted of GSH (FIG. 4B).

Figure 5:
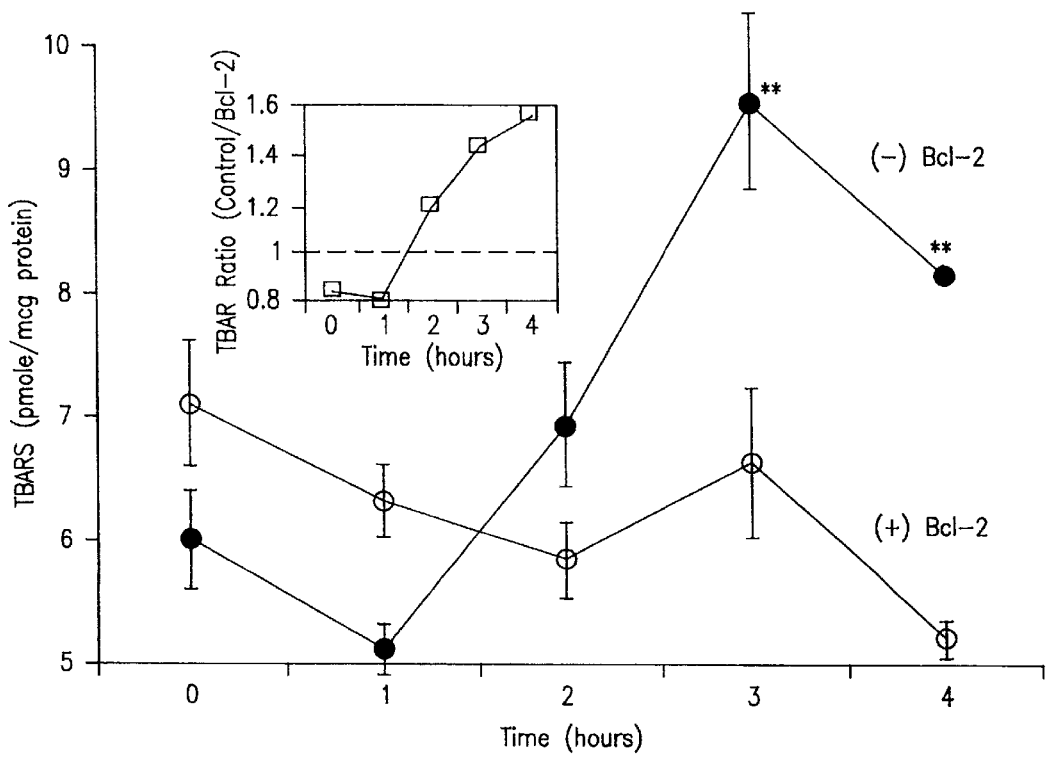
FIG. 5. Expression of bcl-2 prevents lipid peroxidation after GSH depletion. GT1–7 cells were maintained as described in FIG. 1. After the cells were treated with diethyl maleate (1 mM) at 37° C., we assessed lipid peroxidation by determining the quantity of thiobarbituric acid-reactive substances (TBARS) as a measure of malondialdehyde formation (A22). A Cytofluor 2300 plate reader was used to measure fluorescence at 590 nm, with an excitation wavelength of 530 nm. Standard curves were prepared with tetraethoxypropane as a lipoperoxide standard and immunoglobulin as a protein standard. At t=0, 1 and 2 hours no significant differences in TBARS per microgram of protein were detected between control and bcl-2-expressing cells, but at t=3 and 4 hours, highly significant differences occurred. (P<0.0001 by two-way analysis of variance, n=14; indicated by asterisks), both between control (at t=0) and control (at t=3 and 4 hours). The increase in TBARS in control cells preceded cell death, which was 7±1% at t=3 hours and 30±3% at t=4 hours, determined with propidium iodide as in FIG. 2. At no time point did the cells expressing bcl-2 demonstrate a significant rise in thiobarbituric acid-reactive substances in comparison with the value at t=0. (Inset) Ratio of thiobarbituric acid-reactive substances (picomoles per microgram of protein) present in control cells to those present in bcl-2-expressing cells at t=0 to 4 hours, demonstrating a progressing increase.

The diminished net cellular generation of reactive oxygen species in bcl-2-expressing GT1–7 cells depleted of GSH was associated with an inhibition of lipid peroxidation: whereas lipid peroxidation in control cells treated with 1 mM diethyl maleate increased after 2 hours (prior to cell death), no increase in lipid peroxidation occurred in cells expressing bcl-2 (FIG. 5).

To exclude the possibility of the involvement of nitric oxide, the effect of inhibited nitric oxide synthesis with nitro-L-arginine methyl ester (300 $\mu$M) was tested (A14) and the effect of enhanced nitric oxide production induced by S-nitroso-N-acetylpenicillamine (1 $\mu$M) (A 15). In neither case was there a difference between control cells and bcl-2-expressing cells with respect to reactive oxygen species production or cell death.

In accordance with the present invention, the expression of bcl-2 inhibits cell death by decreasing the net cellular generation of reactive oxygen species. This predicts that bcl-2 expression should enhance the growth of cells deficient in superoxide dismutase. Therefore, mutants of the yeast Saccharomyces cerevisiae that carry null mutations for copper-zinc superoxide dismutase (sod1) or manganese superoxide dismutase (sod2) were transformed with an expression construct for bcl-2 or a control construct lacking the coding sequence for bcl-2. As demonstrated previously, sod2 mutants grew poorly under conditions of respiratory metabolism, whereas wild type S. cerevisiae grew well under these conditions (A17). Bcl-2 expression enhanced the growth of sod2 mutants that were grown in 21% $O_2$ under conditions requiring respiratory metabolism, and to a lesser extent, bcl-2 expression enhanced the growth of sod1 mutants in fermentative conditions (18). However, bcl-2 expression did not increase superoxide dismutase activity in the yeast mutants nor enhance the growth of a histidine auxotroph. The procedure used to prepare the yeast mutants was as follows:

An 850-base pair (bp) fragment containing the open reading frame of the human bcl-2 complementary DNA (cDNA) was ligated into the expression vector pAD4 containing the strong promoter of the alcohol dehydrogenase gene and the LEU2 selectable marker, and this construct was used for transformation of yeast. A vector without the 850-bp bcl-2 fragment was used as a control. Four strains of yeast were transformed with the two constructs: the parental strain (DBY746; leu2–3, 11 his3Δ1 trp1-289a ura3-52); sod1 (EG 118; leu2–3, 11 his3Δ1 trp1-298a ura3-52; sod1ΔA::URA3); sod2 (EG110; leu2-3, 11 his3Δ1 trp1-298a ura3-52; sod2Δ::TRP1); and sod1sod2 (G133; leu2–3, 11 his3Δ1 trp1-298a ura3-52; sod1ΔA::URA3 sod2Δ::TRP1). The lithium acetate method was used for transformation (23). After transformation and selection in medium lacking leucine, yeast were quantified by an assay of the optical density at 600 nm, then equal numbers were streaked in each of six plate sections and grown for 5 days in room air or in an atmosphere of 100% $O_2$. As a control, bcl-2 was expressed in a histidine auxotroph; no growth was detected on His⁻ plates. Enhanced growth of sod2 mutants expressing bcl-2 was demonstrated by (i) growth on glycerol plates in 21% $O_2$ (no growth detected for pAD4-transformed sod2 mutants) and (ii) enhanced plating efficiency on glycerol in 21% $O_2$ (0 for pAD4 control compared with $4\times10^3$ for bcl-2-expressing sod2 mutants and $5\times10^5$ for wild-type S. cerevisiae). Enhanced growth of sod1 mutants expressing bcl-2 was demonstrated by (i) growth on dextrose in reduced (~10%) $O_2$ (no growth detected for pAD4-transformed sod1 mutants) and (ii) increased growth in liquid culture; optical densities were compared for sod1 mutants transformed with pAD4 with those transformed with pAD4-bcl-2. After 6 hours in culture, the optical density of the pAD4-transformed sod1 mutants was 4.4, in comparison with 7.2 for those transformed with pAD4 bcl-2.

The involvement of iron [indicated by the protective effect of a concentration of desferrioxamine that has iron-binding but not radical-scavenging properties (100 $\mu$M)] (A12) and hydrogen peroxide (indicated by the effect of catalase inhibition) shows that hydroxyl radicals mediate neural cell death in this system. Bcl-2 expression may decrease the generation or increase the scavenging of reactive oxygen species. The lack of effect of nitro-L-arginine methyl ester and S-nitroso-N-acetylpenicillamine shows that, nitric oxide is not the most important mediator of cell death that is inhibited by bcl-2 expression.

Several mechanisms for the observed inhibition of the net cellular generation of reactive oxygen species by bcl-2 would be compatible with this example: (i) bcl-2 may function as a direct radical-scavenging protein, (ii) bcl-2 may be a metal-binding protein, or (iii) bcl-2 may inhibit the transfer of electrons from complexes I through III to dioxygen in the mitochondrial inner membrane, thus decreasing the formation of superoxide. Any of these models would be compatible with the finding that bcl-2 inhibits apoptosis in cells devoid of functional mitochondrial DNA (A19). This is because extramitochondrial generation of free-radical species represents a significant contribution to the overall cellular generation of such species (A17) and cells lacking functional mitochondrial DNA nevertheless generate reducing equivalents and have incomplete respiratory complexes I, III, and IV (and a complete complex II), making it likely that these cells do generate reactive oxygen species.

EXAMPLE 3

The GT1–7 neural cells described in Example 2 were treated with TPEN in the same manner that the cells were treated with desferrioxamine. The concentration of TPEN was 100 $\mu$M. The viability of bcl-2 expressing cells was 25±10% whereas the viability of the cells not expressing bcl-2 was 60±15%.

EXAMPLE 4

The same procedure as was carried out in Examples 2 and 3 was again followed except that 1 mM BHA (butyrated hydroxy anisole) was substituted for TPEN. The resulting viability of bcl-2 expressing cells was 42±7% whereas the control cells (i.e. non-bcl-2 expressing) had a viability of 61±9%.

Other compounds which showed the above demonstrated reversal in cell viability were oligomycin and dinitrophenol. At a concentration of 20 $\mu$g/ml, oligomycin did not affect the GTI-7 control cells but induced 14% death in bcl-2 expressing cells. At a concentration of 100 $\mu$M, dinitrophenol demonstrated an 84% viability level for the control cells against a 65% viability level for bcl-2 expressing cells.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments illustrated herein, but is only limited by the following claims.

BIBLIOGRAPHY

1. Tsujimoto, Y., Finger, L., Yunis, J., Nowel, P. & Croce, C. (1984) *Science* 226, 1097–1099.
2. Hockenbery, D., Nuñiez, G., Milliman, C., Schreiber, R. & Korsmeyer, S. (1990) *Nature* (London) 348, 334–336.
3. Cleary, M. L., Smith, S. D. & Sklar, J. (1986) *Cell* 47, 19–28.
4. Haldar, S., Beatty, C., Tsujimoto, Y. & Croce, C. (1989) *Nature* (London) 342, 195–198.
5. Nunez, G., Loncon, L., Hockenbery, D., Alexander, M., McKearn, J. P. & Korsmeyer, S. J. (1990) *J. Immunol.* 144, 3602–3610.
6. Zhong, L. T., Mah, S. P., Edwards, R. H. & Bredesen, D. E. (1992) *Soc. Neurosci. Abstr.* 18, 44.
7. Mah, S. P., Zhong, L. T., Liu, Y., Roghani, A., Bredesen, D. E. & Edwards, R. H. (1993) *J. Neurochem.* 60, 1183–1186.
8. Garcia, I., Martinou, I., Tsujimoto, Y. & Martinou, J. C. (1992) *Science* 258, 302–304.
9. Durand, M., Chugani, D. C., Mahmoudi, M. & Phelps, M. E. (1990) *Soc. Neurosci, Abstr.* 16, 40.
10. Carson, D., Seto, S., Wasson, D. & Carrera, C. (1986) *Exp. Cell. Res.* 164, 273–281.
11. Cheng, B. & Mattson, M. P. (1991) *Neuron* 7, 1031–1041.
12. Bellomo, G., Jewell, S. A., Thor, H. & Orrenius, S. (1982) *Proc. Natl. Acad. Sci. USA* 79, 6842–6846.
13. Masaki, N., Kyle, M. & Farber, J. L. (1989) *Arch. Biochem. Biophys.* 269, 390–399.
14. Verity, M. A., Sarafian, T. S., Guerra, W., Ettinger, A. & Sharp, J. (1990) *Neurotoxicity* 11, 415–26.
15. Charles, A. C., Merrill, J. E., Dirksen, E. R. & Sanderson, M. J. (1991) *Neuron* 6 983–992.
16. Morgenstern, J. P. & Land. H. (1990) *Nucleic Acids Res.* 18, 3587–3596.
17. Alnemri, E. S., Robertson, N. M., Fernandes, T. F., Croce, C. M. & Litwack, G. (1992) *Proc. Natl. Acad. Sci. USA* 89, 7295–7299.
18. Mirabelli, F., Salis, A., Perotti, M., Taddei, F., Bellomo, G. & Orrenius, S. (1988) *Biochem. Phannacol.* 37, 3423–3427.
19. Kerr, J. F. R. & Harmon, B. V. (1991) Apoptosis 3, 321.
20. Martin, D. P., Schmidt, R. E., deStefano, P. S., Lowry, O. H., Carter, J. G. & Johnson, E. M. (1988) *J. Cell Biol* 106, 829–844.
21. Barres, B. A., Hart, I. K., Coles, H. S. R., Burne, J. F., Voyvodic, J. T., Richardson, W. D. & Raff, M. C. (1992) *Cell* 70, 31–46.
22. McConkey, D. J., Hartzell, P., Nicotera, P. & Orrenius, S. (1989) *FASEB J.* 3, 1843–1849.
23. Compton, M. M., Haskill, J. S. & Cidlowski, J. A. (1988) *Endocrinology* 122, 2158–2164.
24. Choi, D. (1988) *Neuron* 1, 623–24.
25. Wyllie, A. H., Morris, R. G., Smith, A. L. & Dunlop, D. (1984) *J. Pathol* 142, 66–77.
26. Kure, S., Tominaga, T., Yoshimoto, T., Tada, K. & Narisawa, K. (1991) *Biochem. Biophys. Res. Commun.*, 179, 39–45.
27. Roberts-Lewis, J. M., Marcy, V. R., Zhao, Y., Fedora, T., Lewis, M. E., Siman, R. & Vaught, J. L. (1992) *Soc. Neurosci. Abstr.* 18, 44.
28. Ignatowicz, E., Vezzani, A. M., Rizzi, M. & D'Incalci, M. (1991) *Neuroreport* 11, 651–654.
29. D'Mello, S. R. & Galli, C. (1992) *Soc. Neurosci. Abstr.* 18, 44.
30. Henderson, S., Rowe, M., Gregory, C., Croom-Carter, D., Wang, F., Longnecker, R., Kieff, E. & Rickinson, A. (1991) *Cell* 65, 1107–1115.
31. Friesen, P. D. & Miller, L. K. (1987) *J. Virol.* 61, 2264–2272.
32. Clem, R. J., Fechheimer, M. & Miller, L. K. (1991) *Science* 254, 1388–1390.
33. Heslot, H. & Gaillardin, C. (1992) *Molecular Biology and Genetic Engineering of Yeasts* (CRC, Boca Raton, Fla), p. 393.
34. Vaux, D. L., Aguila, H. L. & Weissman, I. L. (1992) *Int. Immunol.* 4, 821–824.
35. Tian, Q., Streuli, M., Saito, H., Scholssman, S. & Anderson, P. (1991) *Cell* 67, 629–639.
36. Compton, M. M. & Cidlowski, J. A. (1987) *J. Biol. Chem.* 262, 8288–8292.

A1. L. Zhong et al., *Proc. Natl. Acad. Sci. U.S.A.* 90, 4533 (1933).
A2. S. P. Mah et al., *Neurochem.* 60, 1183 (1993).
A3. P. L. Melton et al., *Neuron* 5, 1 (1990).
A4. O. W. Griffith, *J. Biol. Chem.* 257, 13704 (1982).
A5. Intentionally left blank.
A6. D. C. Shrieve, E. A. Bump, G. C. Rise, *J. Biol. Chem.* 263 14107 (1988). There is a linear relationship between the monochlorobimane fluorescence intensity and the intracellular concentration of GSH.
A7. R. H. Ku and R. E. Billings, *Arch. Biochem. Biophys.* 247, 183 (1986).
A8. O. W. Griffith and A. Meister, *Proc. Natl. Acad. Sci. U.S.A.* 82, 4668 (1985).
A9. M. J. Meredith and D. J. Reed, *J. Biol. Chem.* 257, 3747 (1982).
A10. Intentionally left blank.
A11. A. R. Rosenkranz et al., *J. Immunol. Meth.* 156, 39 (1992).
A12. I. Morel et al., *Free Radical Biol. Med.* 13, 499 (1992).
A13. P. E. Starke and J. L. Farber, *J. Biol. Chem.* 260, 86 (1985).
A14. R. G. Kilbourn et al., *Biochem. Biophys. Res. Commun.* 172, 1132 (1990).
A15. U. C. Garg and A. Hassid, *J. Clin. Invest.* 83, 1774 (1989).
A16. Intentionally left blank.
A17. E. B. Gralla and D. J. Kosman, *Adv. Gen.* 30, 251 (1992).
A18. Intentionally left blank.
A19. M. D. Jacobson et al. *Nature* 361, 365 (1993).
A20. M. B. Hansen, S. E. Nielsen, K. Berg, *J. Immunol Meth.* 119, 203 (1989).
A21. W. L. Richards et al. *Exp. Cell Res.* 159, 235 (1985).
A22. K. Yagi, *Biochem. Med.* 15, 212 (1976).
A23. H. Ito, Y. Fukuda, K. Murata, A. Kimura, *J. Bacteriol.* 153, 163 (1983).

What is claimed is:

1. A method for inhibiting proliferation of cells that endogenously produce bcl-2 protein, said method comprising:

administering to the cells an amount of one or more agents effective to impair the reactive oxygen species limiting-activity of bcl-2 in the cells, and subjecting the cells to a cellular insult that triggers spontaneous production of lethal levels of intracellular reactive oxygen species in the cells, wherein the agent and the cellular insult are different treatments, whereby proliferation of the cells so treated is inhibited as compared to that of untreated cells exposed to the cellular insult.

2. The method according to claim 1 wherein the agent is selected from the group consisting of metal chelators and reducing agents.

3. The method according to claim 2 wherein the metal chelator is N,N,N',N'-tetrakis(2-pyridylmethyl) ethylenediamine or desferrioxamine.

4. The method according to claim 2 wherein the reducing agent is butylated hydroxyanisole or butylated hydroxytoluene.

5. The method according to claim 1 wherein the cells are cancer cells.

6. The method according to claim 5 wherein the cancer cells are selected from the group consisting of prostate carcinoma, neuroblastoma, and B-cell lymphoma.

7. The method according to claim 1 wherein the method is carried out in vivo by administering the agent to a subject in need thereof.

8. The method according to claim 7 wherein the administering is parenterally or orally.

9. A method according to claim 1 wherein said method is carried out in vitro.

10. A method for inhibiting proliferation of cells that endogenously produce bcl-2 protein, said method comprising administering to the cells an amount of a first agent effective to inhibit the ability of the bcl-2 to reduce the number of reactive oxygen species in the cells, subjecting the cells to a cellular insult that triggers spontaneous production of lethal levels of intracellular reactive oxygen species in the cells, wherein the first agent and the cellular insult are different treatments, and administering to the cells a second, chemotherapeutic agent, whereby the proliferation of the cells so treated is inhibited as compared with that of untreated cells exposed to the cellular insult.

11. The method according to claim 10 wherein the first agent is selected from the group consisting of metal chelators, and reducing agents.

12. The method according to claim 11 wherein the metal chelator is N,N,N',N'-tetrakis(2-pyridylmethyl) ethylenediamine or desferrioxamine.

13. The method according to claim 11 wherein the reducing agent is butylated hydroxyanisole or butylated hydroxytoluene.

14. The method according to claim 10 wherein the cells are cancer cells.

15. The method according to claim 14 wherein the cancer cells are selected from the group consisting of prostate carcinoma, neuroblastoma, and B-cell lymphoma.

16. The method according to claim 10 wherein the method is carried out in vivo by administering the first and second agents to a subject in need thereof.

17. The method according to claim 16 wherein the administering is parenterally or orally.

18. A method according to claim 10 wherein said method is carried out in vitro.

* * * * *